United States Patent [19]
Farkas et al.

[11] 4,092,346
[45] May 30, 1978

[54] ACYL-PHENOXY-PROPANESULFOACIDS AND SALTS, AND ARTIFICIAL SWEETENING COMPOSITIONS CONTAINING THE SAME

[75] Inventors: Lóránd Farkas; Mihály Nógrádi; Tódor Pfliegel; Sándor Antus; Agnes Gottsegen, all of Budapest, Hungary

[73] Assignee: Chinoin Gyógyszer és Vegyészeti Termékek Gyára Rt., Budapest, Hungary

[21] Appl. No.: 746,350

[22] Filed: Dec. 1, 1976

Related U.S. Application Data

[63] Continuation of Ser. No. 550,659, Feb. 18, 1975, abandoned.

[30] Foreign Application Priority Data

Feb. 19, 1974 Hungary .......................... OE 1448

[51] Int. Cl.² ..................... C07C 143/24; A23L 1/236
[52] U.S. Cl. .................................. 260/511; 426/548
[58] Field of Search ........................................ 260/511

[56] References Cited

U.S. PATENT DOCUMENTS

| 3,522,236 | 7/1970 | Krbechek et al. | 260/210 |
| 3,739,064 | 6/1973 | Rizzi | 424/49 |
| 3,787,442 | 1/1974 | Wendt et al. | 260/327 TH |
| 3,826,856 | 7/1974 | Horowitz et al. | 426/213 |
| 3,956,375 | 5/1976 | Farkas et al. | 260/520 C |
| 3,974,299 | 8/1976 | Crosby et al. | 260/511 |
| 3,976,687 | 8/1976 | Crosby et al. | 260/511 |

Primary Examiner—James O. Thomas, Jr.
Assistant Examiner—G. T. Breitenstein
Attorney, Agent, or Firm—Karl F. Ross

[57] ABSTRACT

Compounds of the formula (1), or their salts,

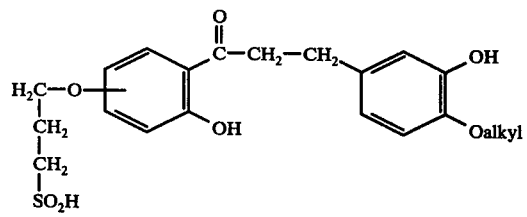

are prepared as follows:
(a) a compound of the formula (II)

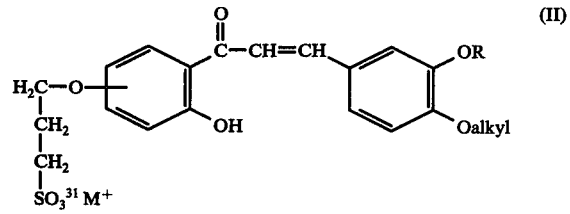

is reduced; or
(b) a compound of the formula (III)

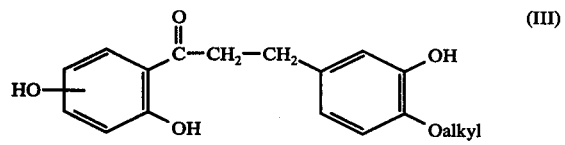

is reacted, e.g. after protecting the phenolic hydroxy group attached to position 3 of the ring, with a compound of the formula (IV),

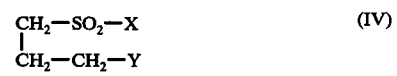

or
(c) group $R^1$ of a compound of the formula (V)

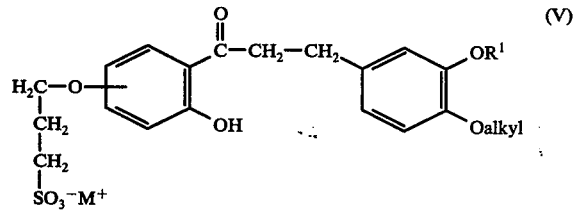

is removed in an acidic medium,
and, if desired, the compound of the formula (I) is converted into salt, or a salt of a compound of the formula (I) is converted into the free acid or another salt thereof.

The compounds of the formula (I) and their salts are valuable artificial sweetening agents.

In the above formulae
"alkyl" is a $C_{1-4}$ alkyl group,
R is hydrogen or a protecting group capable of splitting off upon hydrogenolysis, preferably benzyl or benzyloxycarbonyl,
M+ is a proton or another cation,
X is a group of the general formula $O^-M^+$,
Y is halogen, or
X and Y together represent an oxygen atom, and
$R^1$ is a protecting group capable of splitting off in acidic media, such as 2-tetrahydropyranyl or 1-ethoxyethyl.

5 Claims, No Drawings

ACYL-PHENOXY-PROPANESULFOACIDS AND SALTS, AND ARTIFICIAL SWEETENING COMPOSITIONS CONTAINING THE SAME

This is a continuation of Ser. No. 550,659 filed 18 Feb. 1975, now abandoned, which was copending with Ser. No. 311,666, now U.S. Pat. No. 3,956,375.

This invention relates to new acyl-phenoxy-propanesulfoacids and salts and to artificial sweetening compositions containing the same.

As known, artificial sweeteners without high caloric value are essential both for diabetics and healthy persons of excess body weight. As artificial sweeteners, cyclamates and saccharin have been commonly used in recent practice. Although the use of cyclamates is prohibited in some countries, and the saccharin substances have steadily lost in importance owing to their unpleasant after-taste, no other artificial sweetening agent equivalent to these compounds has been widely marketed so far. Several saccharin-type compositions are known in which the favorable sweetening ability of saccharin is utilized, and the unpleasant after-taste is suppressed with sugar or other additives rich in caloric value. Thus, for instance, U.S. Pat. No. 3,743,518 describes a mixture in which 1 part by weight of calcium saccharide or sodium saccharide is mixed with about 5 parts by weight of fructose and 10 to 15 parts by weight of calcium or sodium gluconate or glucono-δ-lactone, respectively. U.S. Pat. No. 3,087,821 describes hesperetin-dihydrochalcon-glucoside as a compound with an intense sweet taste and applicable as artificial sweetener, and U.S. Pat. No. 3,429,873 describes the preparation of these compounds from the hesperetine-like natural flavononglucosides occurring in citrus fruits. The extremely specific nature of sweet taste is reflected by the fact that hesperetine-dihydochalcon-rhutinoside is a tasteless substance, whereas the glucoside formed by splitting an L-rhamnose molecule from this compound has a sweetening value equivalent to that of saccharin. The preparation of dihydrochalcon-alkoxycarboxylic acid derivatives and their salts is described in Hungarian patent specification No. 163,394.

This invention relates to acyl-phenoxy-propanesulfoacids of the formula (I),

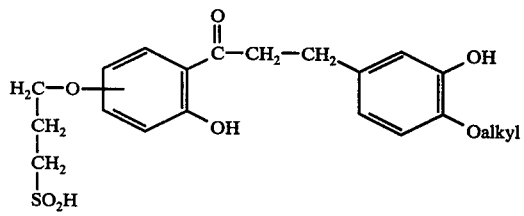

wherein "alkyl" stands for a $C_{1-4}$ alkyl group, and to the salts thereof.

These compounds are highly soluble, thermally stable, resistant to the action of acids, and non-toxic. They have high sweetening values, and have no unpleasant by-flavor. Thus these compounds, optionally in combination with additives, various salts or other sweetening agents, can be applied to great advantage for sweetening foodstuffs, pharmaceuticals, etc. As the additives for the compounds of formula (I), e.g. diluents, solvents, carriers, substances promoting the impression of sweet taste, etc. can be used, either alone or in combination with each other. The invention also relates to a method for flavoring (sweetening) foodstuffs and pharmaceuticals.

The most preferred group of the new compounds having the formula (I) is the following:

1-(2-hydroxy-4-[3-sulfo-propyl-1-oxy]-phenyl)-3-(3-hydroxy-4-methoxyphenyl)-propane-1-one and salts thereof, 1-(2-hydroxy-4-[3-sulfo-propyl-1-oxy]-phenyl)-3-(3-hydroxy-4-ethoxyphenyl)-propane-1-one and its salts, 1-(2-hydroxy-5-[3-sulfo-propyl-1-oxy]-phenyl)-3-(3-hydroxy-4-methoxy-phenyl)-propane-1-one and its salts and 1-(2-hydroxy-5-[3-sulfo-propyl-1-oxy]-phenyl)-3-(3-hydroxy-4-ethoxyphenyl)-propane-1-one and its salts.

These compounds can be prepared in accordance with the invention by any of the following process variants:

(a) a compound of the formula (II):

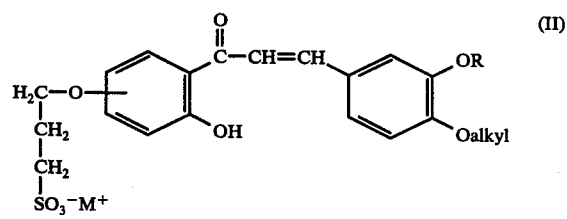

wherein
"alkyl" is for a $C_{1-4}$ alkyl group,
R is hydrogen or a protecting group capable of being split off upon hydrogenolysis, such as benzyl or benzyloxycarbonyl, and
$M^+$ is a proton or another cation, is reduced; or (b) a compound of the formula (III):

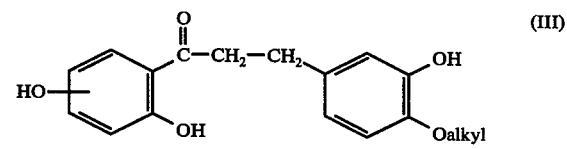

wherein "alkyl" has the same meaning as given above, is reacted, e.g. after protecting the phenolic hydroxy group attached to position 3 of the ring, with a compound of the formula (IV),

wherein X is a group of the formula $O^-M^+$ and Y is halogen, or X and Y together represent an oxygen atom; or (c) group $R^1$ of a compound of the formula (V),

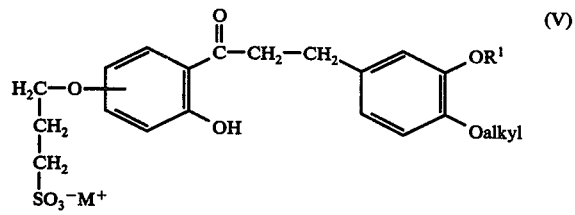

wherein R¹ is a protecting group capable of being split off in acidic media, such as 2-tetrahydropyranyl or 1-ethoxyethyl, and M⁺ and "alkyl" each have the same meanings as given above, is removed in an acidic medium;

and, if desired, a compound of the formula (I) is converted to its salt, or a salt of a compound of the formula (I) is converted into the free acid or another sweetening salt thereof.

When M⁺ stands for a cation, it represents preferably an alkali metal (such as sodium or potassium), an alkaline-earth metal (such as calcium or magnesium) or ammonium ion.

When Y stands for halogen, it represents preferably chorine, bromine or iodine.

In Method variant (a) of the invention, a compound of the formula (II) is reduced preferably by catalytic hydrogenation. As the catalyst, e.g. palladium, preferably supported on carbon, platinum, or Raney-nickel can be used. The hydrogenation is performed in a solvent, preferably water, at room temperature or with heating, under atmospheric or superatmospheric pressure.

In Method variant (b) of the invention, a compound of the formula (III) is reacted with a compound of the formula (IV) either at room temperature in the presence of a solvent, preferably water or dimethylformamide, or by fusing the reactants in the absence of solvent. In both instances an acid-binding agent, preferably an alkali metal hydroxide, carbonate or hydrocarbonate, is added to the reaction mixture. As the reactant of the formula (IV), preferably propanesultone or a 3-halo-1-propanesulfonic acid, or a salt thereof can be used.

In Method variant (c) of the invention, the protecting group is split off preferably in a hydrochloric acid medium.

The starting substances of the above process variants can be prepared as follows:

The compounds of the formula (II) can be prepared by condensing a salt of a sulfoacid of the formula

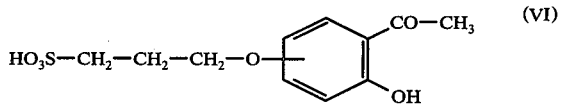

(VI)

with a compound of the formula (VII),

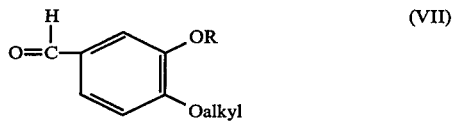

(VII)

wherein R and "alkyl" each have the same meanings as defined above. The condensation is carried out at room temperature, in the presence of an aqueous solution of an alkali metal hydroxide, preferably sodium or potassium hydroxide. According to another method, the compounds of the formula (II) can be prepared by reacting a compound of the formula (VIII),

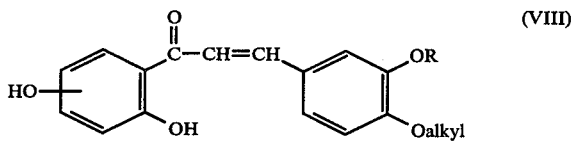

(VIII)

wherein R and "alkyl" each have the same meanings as defined above, with a compound of the formula (IV). This reaction is carried out at room temperature in a solvent, preferably water, in the presence of an acid-binding agent, such as an alkali metal hydroxide, carbonate or bicarbonate.

The compounds of the formula (III), used as starting substances according to Method variant (b), can be prepared by reducing the corresponding compounds of the formula (VIII). The reduction is performed preferably by catalytic hydrogenation in a solvent, particularly water, at room temperature or with heating.

The salts of the acyl-phenoxy-propanesulfoacids of the formula (I) can be prepared by neutralizing the free acid with an oxide or hydroxide of the appropriate metal, or with a salt of the metal formed with a weak acid, preferably with its carbonate or bicarbonate. The salts can also be converted into salts formed with other metal ions. In this instance preferably a poorly water-soluble salt of the acid of the formula (I), such as the calcium salt, is prepared first, and then this salt is treated with the sulfate of the appropriate metal. The calcium sulfate by-product is removed by filtration, and the obtained salt is separated from the aqueous solution preferably by evaporation or direct crystallization.

The invention is elucidated in further detail in the following Examples.

EXAMPLE 1

10 g. of sodium bicarbonate are added to a suspension of 15.2 g. of 2,4-dihydroxyacetophenone in 30 ml. of water, and the mixture is heated cautiously until a homogeneous solution is obtained. The reaction mixture is cooled to 0° C; on cooling, the salt of the acetophenone reactant separates. Propanesulfone is added to the suspension in an amount corresponding to 6.8 g. of pure substance; during this operation the mixture is vigorously stirred. The mixture is stirred at about 0° C for 2 hours, and then heated on a steam bath for 15 minutes. The optionally acidic solution is neutralized, and thereafter acidified to pH = 2 with concentrated hydrochloric acid. The mixture is cooled to 0° C, the separated product is filtered off, washed with a few amount of ice water, dried, then suspended in acetone, filtered again, and dried. 10.5 g. (72%) of 2-hydroxy-4-(3-sulfo-propyl-1-oxy)-acetophenone sodium salt are obtained; m.p.: > 300° C.

EXAMPLE 2

A mixture of 5.0 g. of the 2-hydroxy-4-(3-sulfo-propyl-1-oxy)-acetophenone sodium salt (Example 1), 2.6 g. of isovanillin and 17 ml. of 8 N sodium hydroxide solution is stirred at room temperature for 48 hours. The yellow suspension is acidified with 10% hydrochloric acid, the separated substance is filtered off, suspended in 50 ml. of acetone, filtered off again, and dried. 6.0 g. (82%) of 2',3-dihydroxy-4-methoxy-4'-(3-sulfopropyl-1-oxy)-chalcon sodium salt are obtained; m.p.: 273°–276° C. If desired, this product can be purified further by recrystallization from water.

EXAMPLE 3

A mixture of 14.4 g. of 2-hydroxy-4-(3-sulfo-propyl-1-oxy)-acetophenone sodium salt, 8.0 g. of 3-hydroxy-4-ethoxybenzaldehyde and 60 ml. of a 8 N sodium hydroxide solution is stirred at room temperature for 96 hours. The yellow suspension is acidified with 10% hydrochloric acid, the separated crude product is filtered off, and recrystallized twice from water. 6.0 g. (28%) of 2′,3-dihydroxy-4-ethoxy-4′-(3-sulfo-propyl-1-oxy)-chalcon sodium salt are obtained. The product shrinks at 250° C without melting.

EXAMPLE 4

A solution of 5.0 g. of 2′,3-dihydroxy-4-ethoxy-4′-(3-sulfo-propyl-1-oxy)-chalcon sodium salt (Example 3) in 50 ml. of water is hydrogenated at 60° C, in the presence of 1 g. of palladium/carbon catalyst, until the uptake of the calculated amount of hydrogen. The mixture is filtered, the filtrate is evaporated to dryness, and the residue is recrystallized twice from a minimum amount of water. 2.0 g. (40%) of 1-(2-hydroxy-4-[3-sulfonyl-propyl-1-oxy]-phenyl)-3-(3-hydroxy-4-ethoxyphenyl)-propanone-1 are obtained; m.p.: 239°–241° C (decomposition).

EXAMPLE 5

A solution of 20 g. of 1-(2-hydroxy-4-[3-sulfo-propyl1-oxy]-phenyl)-3-(3-hydroxy-4-methoxyphenyl)-prop-2-ene-1-one sodium salt in 100 ml. of water is hydrogenated at 60° C in the presence of 4 g. of palladium/carbon until the uptake of the calculated amount of hydrogen. The mixture is heated to 95° C, the catalyst is filtered off, and the filtrate is cooled. The separated substance is filtered off, washed with a small amount of ice water, and dried. 13 to 14 g. (65 to 70%) of 1-(2-hydroxy-4-[3-sulfo-propyl-1-oxy]-phenyl)-3-(3-hydroxy-4-methoxyphenyl)-propanone-1 are obtained; m.p.: 257°–258° C (decomposition).

EXAMPLE 6

10 g. of 1-(2-hydroxy-4-[3-sulfo-propyl-1-oxy]-phenyl)-3-(3-benzyloxy-4-methoxyphenyl)-prop-2-ene-1-one are added to pre-hydrogenated palladium/carbon catalyst in 50 ml. of water, and the obtained suspension is stirred at 60° C until the uptake of 2 molar equivalents of hydrogen. The solution is filtered when hot, and the filtrate is cooled. 7.0 g. of 1-(2-hydroxy-4-[3-sulfo-propyl-1-oxy]-phenyl)-3-(3-hydroxy-4-methoxyphenyl)-propanone-1 are obtained.

EXAMPLE 7

10 g. of 1-(2-hydroxy-4-[3-sulfo-1-propyl-1-oxy]-phenyl)-3-(3-[2-tetrahydropyranyloxy]-4-methoxyphenyl)-prop-2ene-1-one are added to palladium/carbon catalyst pre-hydrogenated in 50 ml. of water, and the obtained suspension is stirred at 60° C until the uptake of one molar equivalent of hydrogen. The catalyst is removed by filtration, 1 ml. of concentrated hydrochloric acid is added to the filtrate, and the mixture is heated at 90° C for 20 minutes. On cooling, 6.5 g. of 1-(2-hydroxy-4-[3-sulfo-propyl-1-oxy]-phenyl)-3-(3-hydroxy-4-methoxyphenyl)-propanone-1 separate from the solution.

EXAMPLE 8

7.2 g. of 1-(2,4-dihydroxyphenyl)-3-(3-[2-tetrahydropyranyloxy]-4-methoxyphenyl)-propanone-1 are dissolved in 22 ml. of a 1 N sodium hydroxide solution, and 2.68 g. of propanesulfone are added to the solution in portions within one hour. The solution is heated on a steam bath for 15 minutes, thereafter 2 ml. of concentrated hydrochloric acid are added, and heating is continued for additional 20 minutes. The solution is filtered when hot, and the filtrate is cooled. 4.0 g. of 1-(2-hydroxy-4-[3-sulfo-propyl-1-oxy]-phenyl)-3-(3-hydroxy-4-methoxyphenyl)-propanone-1 are obtained.

EXAMPLE 9

The sodium salt of 1-(2-hydroxy-4-[3-sulfo-propyl-1-oxy]-phenyl)-3-(3-hydroxy-4-methoxyphenyl)-propanone-1 can be converted into other salt. via the poorly soluble calcium alt. An excess of a calcium chloride solution is added to the warm, concentrated aqueous solution of the sodium salt, the separated calcium salt is filtered off, washed sodium-free, then suspended in hot water, and an equivalent amount of the sulfate of the appropriate metal is added. The suspension is stirred with heating for about one-half hour, the separated calcium sulfate is removed by filtration, and the filtrate is evaporated, or the obtained salt is allowed to crystallize, respectively.

What we claim is:

1. A compound of the formula (I),

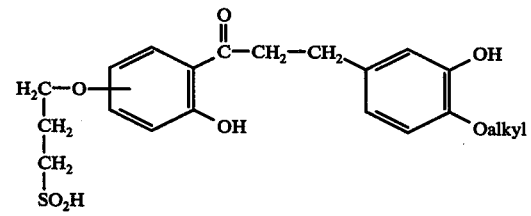

wherein "alkyl" is a $C_{1-4}$ alkyl group or an alkali metal, alkaline-earth metal or ammonium salt thereof.

2. 1-(2-Hydroxy-4-[3-sulfo-propyl-1-oxy]-phenyl)-3-(3-hydroxy-4-methoxyphenyl)-propanone-1 or its salts, as defined in claim 1.

3. 1-(2-Hydroxy-4[3-sulfo-propyl-1-oxy]-phenyl)-3-(3-hydroxy-4-ethoxyphenyl)-propanone-1 or its salts, as defined in claim 1.

4. 1-(2-Hydroxy-5-[3-sulfo-propyl-1-oxy]-phenyl)-3-(3-hydroxy-4-methoxyphenyl)-propanone-1 or its salts, as defined in claim 1.

5. 1-(2-Hydroxy-5-[3-sulfo-propyl-1-oxy]-phenyl)-3-(3-hydroxy-4-ethoxyphenyl)-propanone-1 or its salts, as defined in claim 1.

* * * * *